US012133957B2

United States Patent
Wills

(10) Patent No.: US 12,133,957 B2
(45) Date of Patent: Nov. 5, 2024

(54) INDWELLING "FOLEY" CATHETER CAP

(71) Applicant: Robert Patrick Wills, Minneola, FL (US)

(72) Inventor: Robert Patrick Wills, Minneola, FL (US)

(73) Assignee: Robert P. Wills, Minneola, FL (US)

(*) Notice: Subject to any disclaimer, the term of this patent is extended or adjusted under 35 U.S.C. 154(b) by 246 days.

(21) Appl. No.: 17/355,315

(22) Filed: Jun. 23, 2021

(65) Prior Publication Data
US 2022/0409853 A1      Dec. 29, 2022

(51) Int. Cl.
A61M 25/00       (2006.01)
A61M 25/01       (2006.01)

(52) U.S. Cl.
CPC ........ *A61M 25/0017* (2013.01); *A61M 25/01* (2013.01)

(58) Field of Classification Search
CPC .............. A61M 25/0017; A61M 25/02; A61M 2025/024; A61M 2025/0266; A61M 2210/1078; A61M 2210/1085; A61M 2210/1089; A61M 2210/1096; A61M 25/01
See application file for complete search history.

(56) References Cited

U.S. PATENT DOCUMENTS

| | | | | | |
|---|---|---|---|---|---|
| 2,213,210 | A | * | 9/1940 | Egbert | A61F 5/453 604/179 |
| 2,547,758 | A | * | 4/1951 | Keeling | A61M 25/10 D24/112 |
| 3,605,752 | A | * | 9/1971 | Schlesinger | A61M 25/02 604/289 |
| 3,848,603 | A | * | 11/1974 | Throner | A61L 29/16 604/247 |
| 4,337,775 | A | * | 7/1982 | Cook | A61M 25/10 604/284 |

(Continued)

FOREIGN PATENT DOCUMENTS

| | | | |
|---|---|---|---|
| CN | 201337559 Y | * | 11/2009 |
| CN | 203107958 U | * | 8/2013 |

(Continued)

OTHER PUBLICATIONS

CN 203107958 U, Google Patents machine translation, Oct. 27, 2023. (Year: 2023).*

*Primary Examiner* — Adam Marcetich

(57) ABSTRACT

The Foley Catheter Cap molded from medical grade silicone to provide a stable base for the insertion of an indwelling "Foley" catheter so that tearing of the urethra does not occur. Since the head of a penis contains no sweat glands of any kind, there is no buildup of fluids beneath the Foley Catheter Cap to occur which thereby precludes an environment under the Foley Catheter Cap which could be conducive for infections to grow. Because of this the benefits of a Foley Catheter Cap for male patients required to have an indwelling catheter for extended periods of time greatly outweigh any latent risk while the omission of the proposed Foley Catheter Cap exposes male patients to the potential of the well-documented serious injury and follow-on reconstructive surgery caused by Ventral Erosion of the penis.

1 Claim, 2 Drawing Sheets

(56) References Cited

U.S. PATENT DOCUMENTS

| | | | | |
|---|---|---|---|---|
| 4,388,923 A | * | 6/1983 | Heimreid | A61F 5/453 600/580 |
| 4,419,097 A | * | 12/1983 | Rowland | A61M 25/02 604/174 |
| 4,484,918 A | * | 11/1984 | Omley | A61F 5/453 604/349 |
| 4,810,247 A | * | 3/1989 | Glassman | A61M 27/00 604/174 |
| 4,821,742 A | * | 4/1989 | Phelps, III | A61F 6/04 128/842 |
| 4,834,711 A | * | 5/1989 | Greenfield | A61M 25/0111 604/172 |
| 4,963,137 A | * | 10/1990 | Heyden | A61F 5/453 604/349 |
| 5,195,998 A | * | 3/1993 | Abraham | A61F 5/453 604/351 |
| 5,421,350 A | * | 6/1995 | Friedman | A61F 6/04 128/842 |
| 5,620,424 A | * | 4/1997 | Abramson | A61M 25/0111 604/174 |
| 6,035,854 A | * | 3/2000 | Blake | A61F 6/04 128/842 |
| 11,331,212 B1 | * | 5/2022 | Krasnoff | A61F 6/005 |
| 2002/0169438 A1 | * | 11/2002 | Sauer | A61M 25/0111 604/544 |
| 2010/0145314 A1 | * | 6/2010 | Hazan | A61M 25/02 604/544 |
| 2014/0142554 A1 | * | 5/2014 | Conway | A61M 25/02 264/154 |
| 2015/0306352 A1 | * | 10/2015 | Banerian | A61M 25/0662 604/544 |
| 2018/0326184 A1 | * | 11/2018 | Sisco | A61M 25/02 |
| 2021/0128880 A1 | * | 5/2021 | Thomas | A61M 25/0017 |
| 2022/0296854 A1 | * | 9/2022 | Chieffo | A61M 25/01 |

FOREIGN PATENT DOCUMENTS

| | | | | |
|---|---|---|---|---|
| CN | 203970473 U | * | 12/2014 | |
| CN | 105797263 A | * | 7/2016 | A61M 25/10 |
| CN | 106139368 A | * | 11/2016 | |
| CN | 208943187 U | * | 6/2019 | |
| CN | 112472970 A | * | 3/2021 | |
| CN | 113244467 A | * | 8/2021 | A61M 11/00 |
| CN | 110732076 B | * | 10/2021 | A61M 25/02 |
| ES | 2342647 A1 | * | 7/2010 | A61F 5/453 |

* cited by examiner

INDWELLING "FOLEY" CATHETER CAP

1. SUMMARY OF THE INVENTION

This invention relates to the Indwelling Catheter, commonly called a "Foley" Catheter which is supplemented by the invention—a Foley Catheter Cap. The Foley Catheter Cap is in its entirety a medical-grade silicone molded cap which fits entirely over the Glans (head) of a penis. If a foreskin is present, it is retracted to expose the entire penis head, and then the Foley Catheter Cap is applied.

Accordingly, the Foley Cap includes an anatomically-correct positioned hole which allows a catheter tube to enter the urethra without bending or kinking. This centrally located hole is molded slightly smaller than the width of a Foley Catheter so that it provides a secure seal between it and the Foley Catheter Cap. The device enables a Foley Catheter to be inserted through the centrally molded hole in the Foley Catheter Cap then into the patient as normally would be inserted by a medical professional without twisting or crimping.

Once the Foley Catheter has been successful inserted, the Foley Catheter Cap is slid down over the head of the penis relieving any lateral pressure against the patient's urethra by the Foley Catheter. If any tearing does occur, it is first of the Foley Catheter Cap which would allow a medical professional in their routine inspection of the Foley Catheter observe the damage and replace the cap before injury to the patient occurs. It should be noted that while there are eccrine sweat glands, which produce odorless sweat on the penis shaft and apocrine sweat glands, which produce an oilier, odorous sweat on the base of the penis as well as the groin, no sweat glands are found on the head of the penis or inside the foreskin. Due to this physiological fact, there is no chance for a buildup of secretions under the Foley Catheter Cap which could lead to an infection. The invention provides for improved elements thereof in an arrangement for the purposes described that are inexpensive, dependable, and fully effective in accomplishing their indented purposes.

These and other features of the present invention will become readily apparent upon further review of the following specifications and drawings.

2. BACKGROUND OF THE INVENTION

A. Field of the Invention

This invention relates to the Indwelling Catheter, commonly called a "Foley" catheter, and more directly to the well-documented damage that may occur in males when Foley catheters are used for an extended period of time—typically over thirty days.

B. Description of Related Art

The indwelling or Foley catheter is named for its inventor Doctor Frederick Foley, a urologist but patented by the Davol Rubber Company of Providence, Rhode Island with production starting in 1934. An indwelling "Foley" catheter is a catheter that resides in the bladder, inserted through the urethra into the bladder. This catheter can be useful for short and long periods of time. A medical professional inserts an indwelling catheter into the bladder through the urethra where a tiny balloon at the end of the catheter is inflated with saline to prevent the tube from sliding back out of the body. The balloon can subsequently be deflated when the catheter needs to be removed. In male patients, these catheters exit the urethra at the end of the penis. Along with perforation of the bladder and infection, one of the potential risks of the use of a Foley Catheter is of urethral erosion.

In men, the resultant partial-thickness or full-thickness wound can involve a small area of the glans penis or cleave the glans or penile shaft completely, requiring reconstructive surgery or urinary diversion. This severe ventral erosion of the penis is caused by prolonged traction of the unsecured Foley Catheter between the inflated balloon within the patient's bladder and the weight of the urine collection bag. While this injury can be prevented by securing the Foley to the patient with tape or clips ensuring that the drainage system is properly supported, inattentiveness by medical professionals and movement by the patient nevertheless causes this injury to occur.

Inasmuch many articles have been written in peer-reviewed medical journals discussing the damage caused by Foley Catheters. In an article in *Advances in Urology*, an open access journal that provides a forum for urologists, nephrologists, and scientists working in the field of urology, it is proposed that this injury be listed as a 'Never Event'. Never Events in the medical terminology are serious, largely preventable patient safety incidents that should not occur if the available preventative measures have been implemented. None of the articles presented offer a solution beyond increased medical personnel inspections of the catheter and the use of softer latex Foley Catheters to try and minimize these injuries.

Since production of the Foley Catheter began in 1934, no other method besides securing of the tube of an indwelling catheter against the body of a male patient or to his clothing is available to prevent Ventral Erosion. Numerous external "condom" catheters are available however their effectiveness on a flaccid penis or the imbedded penis of an obese patient is not consistent. This is due to the fact that to remain secure on a flaccid penis, a condom catheter either requires them to be constricted on the penis to the point of closing the urethra or held in place with adhesive. The Foley catheter has remained relatively unchanged since 1934; the main changes to the device have been only in the materials used to construct them. The invention described herein finally prevents these 'Never Events' from occurring.

3. BRIEF DESCRIPTION OF THE DRAWINGS

Similar reference characters denote corresponding features consistently throughout the attached drawings.

4. DETAILED DESCRIPTION OF THE PREFERRED EMBODIMENTS

Figure 1:
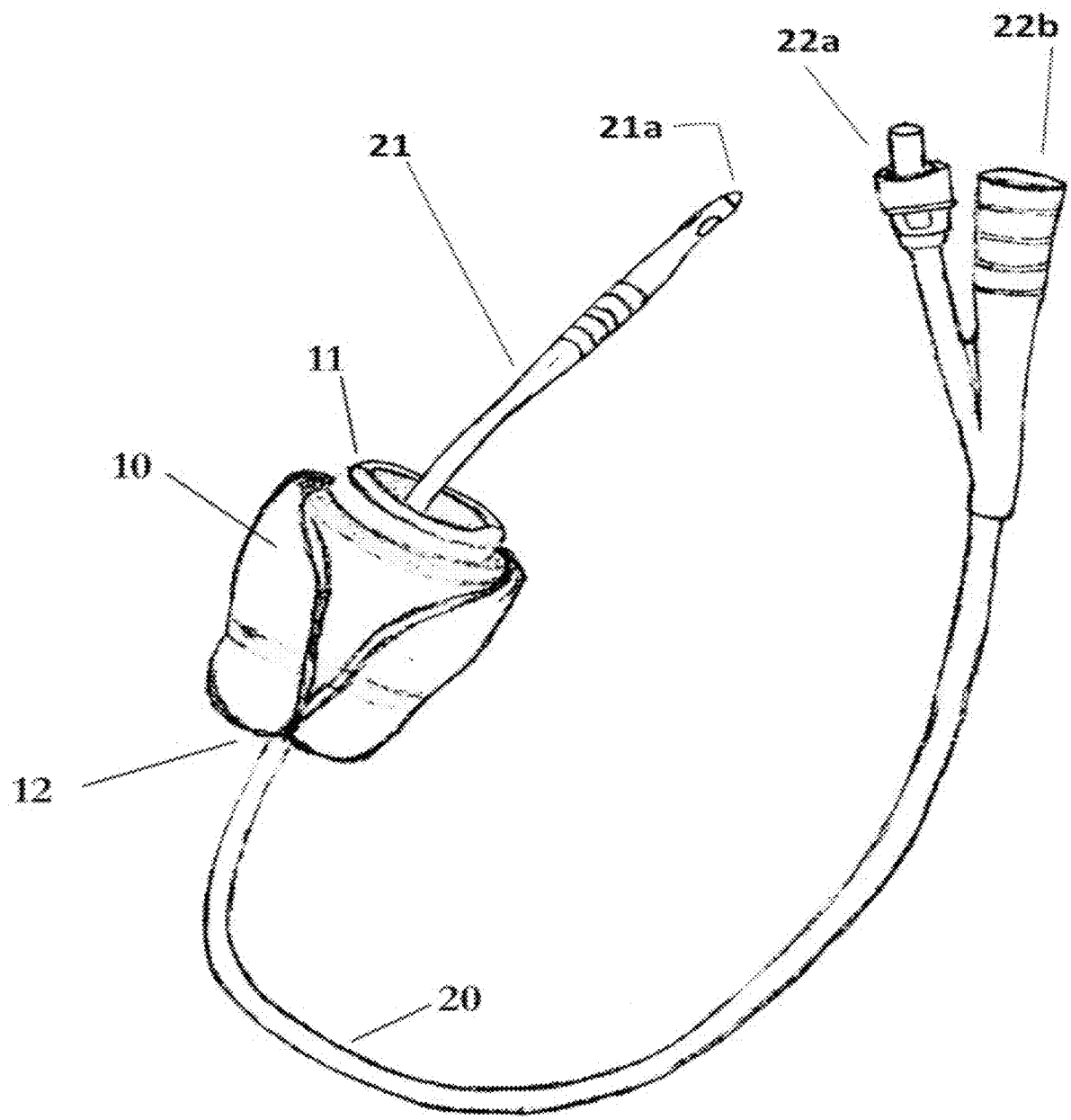
FIG. 1 is an environmental, perspective view of a Foley Catheter Cap with attached Foley Catheter.
Figure 2:
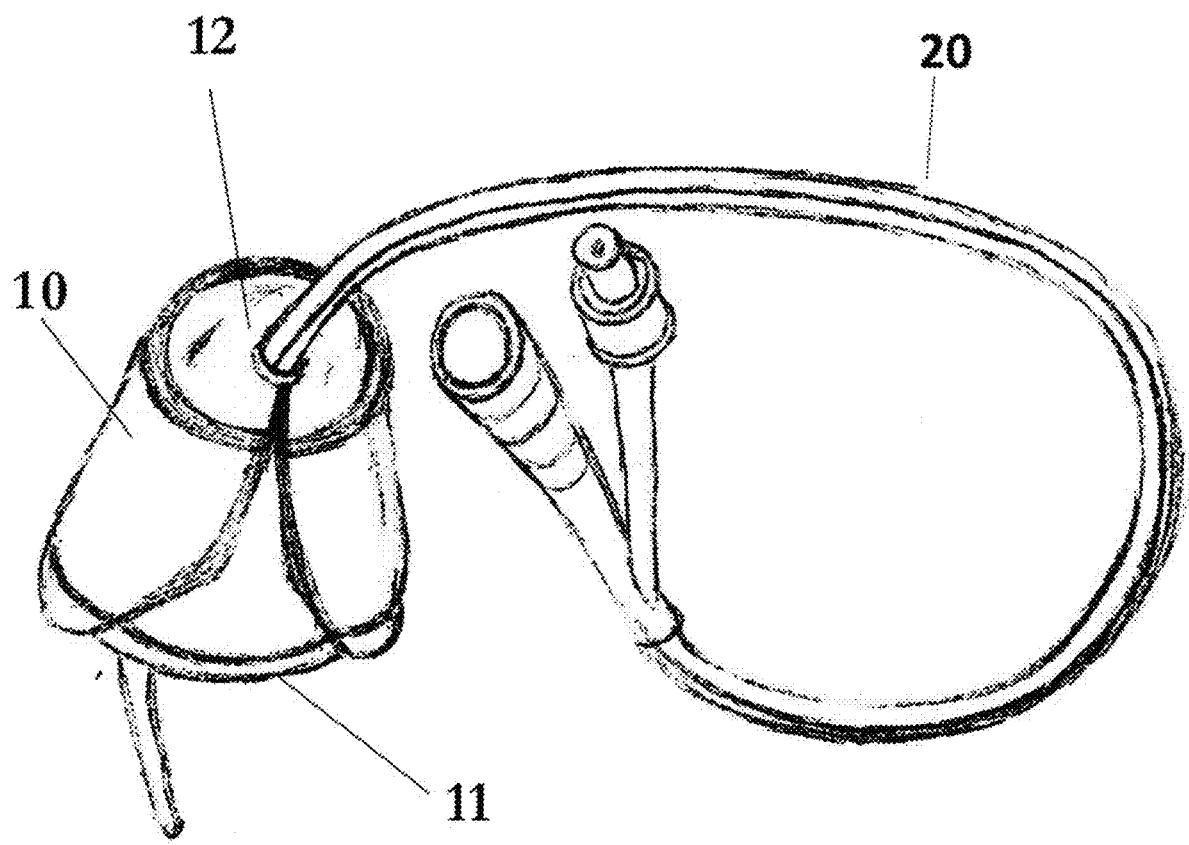
FIG. 2 is a perspective view of a Foley Catheter Cap, showing the position of the anatomically-correct centrally located hole for the Foley Catheter to pass through unhindered.

Referring to FIGS. 1 and 2, a first embodiment of the Foley Catheter Cap 10 comprised of a medical-grade silicone dome-shaped cap 10 to maintain alignment of a Foley catheter tube 20, on a male patient's penis (not shown). Cap 10 remains secured to the Glans (head) of the penis (not shown) by stretching it over the top of the penis head where it is secured behind the head with molded lip 11. In the presence of a foreskin (not shown), the foreskin is pulled back exposing the head in its entirety. Before inserting the catheter into the patient's urethra (not shown) the Foley Catheter 20 is inserted through the hole 12 in the Foley Catheter Cap 10 and the indwelling portion of the Foley Catheter 21 is pulled through to allow sufficient length to insert into the patient.

The dual tubes 22a and 22b on the external portion of the Foley Catheter are used for inflating the securing the indwelling balloon 21a by injecting saline into tube 22a while tube 22b is used for transporting urine out of the bladder.

Referring to FIG. 2, the anatomically-correct positioning of the hole 12 in the Foley Catheter Cap 10 prevents the Foley Catheter tube 20 from becoming misaligned from the urethra (not shown) while the Foley Catheter is inserted through the patient's urethra (not shown) into the bladder (not shown.).

It is also understood that the present invention is not limited to the embodiments described above, but encompasses any and all embodiments within the scope of the claims.

I claim:

1. A detachable Foley catheter cap configured to be attached to a Foley indwelling catheter and to prevent ventral erosion in male patients, comprising:
   a radially asymmetric truncated dome shape;
   wherein the cap comprises an elastic medical grade material;
   a distal opening configured to accept a Foley catheter;
   wherein the cap is configured to contact a penis only at the glans of the penis;
   wherein the radially asymmetric shape comprises an outer portion with a first diameter and an inner portion with a diameter narrower than the first diameter, wherein a pair of contoured edges divide the outer portion from the inner portion; and
   wherein the cap is configured to be anchored solely by an internal molding that projects inward from a proximal opening; and
   wherein the cap lacks any adhesive on its inner surface.

* * * * *